US012569239B1

(12) United States Patent
Stockmans et al.

(10) Patent No.: US 12,569,239 B1
(45) Date of Patent: Mar. 10, 2026

(54) SUTURING PROCEDURE

(71) Applicant: Loci Orthopaedics Limited, Galway (IE)

(72) Inventors: Filip Stockmans, Heule Kortrijk (BE); Brendan Boland, County Kildare (IE); Maria Larkin, Galway (IE)

(73) Assignee: Loci Orthopaedics Limited, Galway (IE)

( * ) Notice: Subject to any disclaimer, the term of this patent is extended or adjusted under 35 U.S.C. 154(b) by 0 days.

(21) Appl. No.: 19/292,419

(22) Filed: Aug. 6, 2025

(51) Int. Cl.
*A61B 17/04* (2006.01)
*A61F 2/42* (2006.01)

(52) U.S. Cl.
CPC ............ *A61B 17/04* (2013.01); *A61F 2/4241* (2013.01); *A61F 2002/4251* (2013.01); *A61F 2002/4256* (2013.01); *A61F 2002/4258* (2013.01); *A61F 2002/4271* (2013.01)

(58) Field of Classification Search
CPC ..... A61B 17/04; A61B 17/0401; A61B 17/56; A61B 17/562; A61B 2017/564; A61B 2017/567; A61F 2/0811; A61F 2/42; A61F 2/4241; A61F 2002/4243; A61F 2002/4253; A61F 2002/4256; A61F 2002/4258; A61F 2002/4271
See application file for complete search history.

(56) References Cited

U.S. PATENT DOCUMENTS

| | | | | |
|---|---|---|---|---|
| 3,745,590 A | * | 7/1973 | Stubstad | A61F 2/4241 128/DIG. 21 |
| 4,450,591 A | * | 5/1984 | Rappaport | A61B 17/562 128/898 |
| 5,702,468 A | * | 12/1997 | Goldberg | A61F 2/4241 623/21.12 |
| 5,743,918 A | * | 4/1998 | Calandruccio | A61F 2/4657 623/908 |
| 2009/0254190 A1 | * | 10/2009 | Gannoe | A61F 2/4261 623/21.11 |
| 2011/0054627 A1 | * | 3/2011 | Bear | A61F 2/4261 623/21.12 |
| 2013/0053897 A1 | * | 2/2013 | Brown | A61B 17/8861 606/232 |
| 2013/0211451 A1 | * | 8/2013 | Wales | A61B 17/0401 606/232 |
| 2013/0231669 A1 | * | 9/2013 | Sinnott | A61B 17/1739 606/86 R |

(Continued)

*Primary Examiner* — Dianne Dornbusch
(74) *Attorney, Agent, or Firm* — Bookoff McAndrews, PLLC

(57) ABSTRACT

A method of suturing a surgical site after implantation, in a carpometacarpal joint of a hand of a patient, of an implant assembly including a first implant having a first suture and a second suture secured to the first implant via a double-loop configuration, the first suture including a first and second suture ends, the second suture including third and fourth suture ends, the surgical site including a capsular flap substantially C-shaped and attached to a trapezial side of the hand, the method including: extending the first and third suture ends in first and second directions across the implant assembly and through first and second punctures, respectively, in the capsular flap; and extending the second and fourth suture ends through the second and first punctures, respectively, where the second and fourth suture ends do not cross over one another or any other suture end.

20 Claims, 7 Drawing Sheets

(56)     References Cited

U.S. PATENT DOCUMENTS

| 2013/0245700 A1* | 9/2013 | Choinski | ........... A61B 17/0401 |
| | | | 606/300 |
| 2014/0128984 A1* | 5/2014 | Jou | ...................... A61F 2/4241 |
| | | | 623/21.15 |
| 2015/0073441 A1* | 3/2015 | Fallin | ................ A61B 17/0482 |
| | | | 606/144 |
| 2018/0280066 A1* | 10/2018 | O'Connor | .......... A61B 17/1615 |
| 2024/0130726 A1* | 4/2024 | Larsen | .............. A61B 17/0401 |

* cited by examiner

SUTURING PROCEDURE

FIELD

The disclosure relates to suturing procedures, and, more specifically, to a suturing procedure used to close a surgical site after implantation of an implant assembly in a patient's carpometacarpal (CMC) joint.

BACKGROUND

A patient may have pain in their thumb, an unstable thumb, or a limited range of thumb movement, for example as a result of the patient suffering from osteoarthritis, rheumatoid arthritis, traumatic arthritis, or post-fracture deformation or bone loss. In such cases, a surgeon may perform surgery, during which the surgeon replaces a portion of the patient's carpometacarpal (CMC) joint with an implant. The implant may alleviate pain in the patient's thumb, stabilize the patient's thumb, and/or restore some range of movement to the patient's thumb.

During surgery, after placing the implant in the patient's CMC joint, the surgeon (or other medical personnel) sutures the surgical site. However, traditional suturing techniques may not adequately stabilize the implant during post-operative healing, and this failure to adequately stabilize the implant may results in a less than optimal outcome. For example, even after surgery and complete post-operative healing, the patient may still experience thumb pain, the patient's thumb still may not be entirely stable, and the patient may not be able to move the thumb through a wide range of movement.

Accordingly, it is desirable to adequately secure the implant within the surgical site during post-operative healing. Adequately securing the implant may alleviate thumb pain and stabilize the thumb to a greater extent, as well as restore a wider range of movement to the thumb.

SUMMARY

In one aspect, the disclosure provides a method of suturing a surgical site after implantation, in a carpometacarpal (CMC) joint of a hand of a patient, of an implant assembly including a first implant having a first suture and a second suture anchored thereto, the first suture and the second suture each secured to the first implant via a double-loop configuration, the first suture and the second suture extending from the first implant, the first suture including a first suture end and a second suture end, the second suture including a third suture end and a fourth suture end, the surgical site including a capsular flap that is substantially C-shaped and attached to a trapezial side of the hand of the patient, the method comprising: extending the first suture end of the first suture in a first direction across the implant assembly and through a first puncture in the capsular flap; extending the third suture end of the second suture in a second direction across the implant assembly and through a second puncture in the capsular flap, such that the first suture end and the third suture end cross over one another; extending the second suture end of the first suture through the second puncture in the capsular flap; and extending the fourth suture end of the second suture through the first puncture in the capsular flap, wherein the second suture end and the fourth suture end do not cross over one another or any other suture end.

In another aspect, the disclosure provides a method of suturing a surgical site after implantation, in a carpometacarpal (CMC) joint of a hand of a patient, of an implant assembly including a first implant implanted in a metacarpal of a patient, a second implant implanted between the first implant and a trapezium of the patient, the first implant having a first suture and a second suture anchored thereto, the first suture and the second suture extending from the first implant, the surgical site including a capsular flap that is substantially C-shaped and attached at a trapezial side of the hand of the patient, the method comprising: extending a suture end of the first suture in a first direction across the second implant and through the capsular flap; extending a suture end of the second suture in a second direction across the second implant and through the capsular flap, such that the suture ends cross over one another; and suturing the capsular flap with at least one suture end of the first suture or at least one suture end of the second suture.

In another aspect, the disclosure provides a method of implanting in a surgical site of a patient, in a carpometacarpal (CMC) joint of a hand of the patient, an implant assembly including a first implant and a second implant, the first implant including a first suture and a second suture anchored thereto, the first suture and the second suture extending from the first implant, the surgical site including a substantially C-shaped capsular flap attached at a trapezial side of the hand of the patient, the method comprising: implanting the first implant into a resected end of a first metacarpal of the patient; implanting the second implant between the first implant and a trapezium of the patient; extending a suture end of the first suture in a first direction across the second implant and through a capsular flap of the patient; and extending a suture end of the second suture in a second direction across the second implant and through the capsular flap of the patient, such that the suture ends cross over one another.

BRIEF DESCRIPTION OF THE FIGURES

The accompanying drawings, which the Specification incorporates such that the figures constitute a part of the Specification, illustrate various exemplary embodiments and together with the description, serve to explain the principles of the disclosure.

DETAILED DESCRIPTION

Figures 1A, 1B:
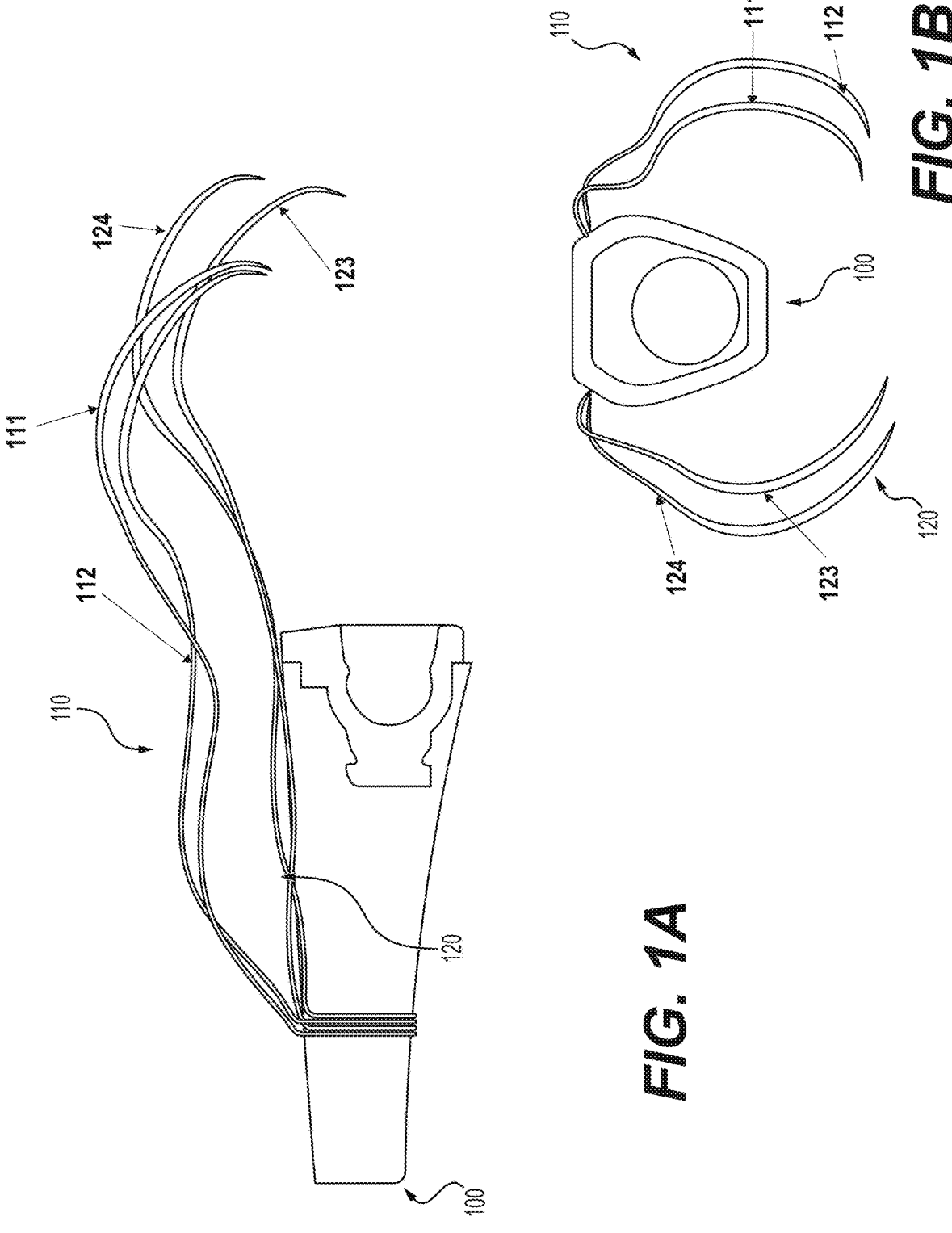
FIGS. 1A and 1B illustrate a side view and an end view, respectively, of part of an implant of an implant assembly, in accordance with some aspects of the disclosure.

Both the foregoing general description and the following detailed description are exemplary and explanatory only, and do not restrict features of the disclosure, as claimed. As used herein, the terms "comprises," "comprising," "has," "having," "includes," "including," and variations thereof, cover a non-exclusive inclusion such that a process, method, article, or apparatus that comprises (for example) a list of elements does not include necessarily only those elements, but instead may include either elements not expressly listed or elements inherent to such a process, method, article, or apparatus. Throughout the Specification, unless stated otherwise, relative terms such as "about," "substantially," and "approximately," and similar terms, indicate a possible variation of ±10% of the stated value.

The meanings of various medical terms throughout the Specification are those meanings as understood by surgeons, doctors, nurses, or other medical personnel.

Although the following description generally refers to "a surgeon," one or more surgeons, doctors, nurses, or other medical personnel may perform one or more portions of the disclosed procedure, including the disclosed suturing procedure.

In accordance with the disclosure, a surgeon may replace a portion of a patient's carpometacarpal (CMC) joint with an implant assembly, the surgeon implanting the implant assembly between the patient's trapezium and a resected end of the patient's first metacarpal, as described below. Thereafter, the surgeon may suture the surgical site, also as described.

A procedure for implanting the implant assembly by a surgeon may include the following. With respect to opening of the surgical site, the surgeon may make an incision into the patient's hand above the patient's CMC joint. For example, the surgeon may make a longitudinal incision into the patient's hand using a dorsal radial approach. The incision may be between approximately 3 cm and approximately 4 cm in length. However, in some instances, the length of the incision may be greater than approximately 4 mm, or less than approximately 3 cm. The incision may extend approximately ⅔ over the patient's first metacarpal, and approximately ⅓ over the patient's trapezium. However, in some instances, the incision may extend more or less than approximately ⅔ over the patient's metacarpal, and and/or more or less than approximately ⅓ over the patient's trapezium. Although the foregoing describes the incision as an apparent first step in a surgical procedure, one or more other steps may proceed the surgeon making the incision. Further, although the following describes additional steps a surgeon may perform, the surgical procedure in accordance with this disclosure need not include all of these steps, and may include additional steps, and may reorder steps.

After the incision described above, the surgeon may make a subsequent incision in the patient's hand between the patient's first dorsal compartment (which includes the patient's extensor pollicis brevis (EPB) and abductor pollicis longus (APL)) and the patient's extensor pollicis longus (EPL). The subsequent incision may be a longitudinal incision. A depth of the subsequent incision may be greater than a depth of the previous incision. Both the subsequent incision and the previous incision may avoid the patient's radial artery, which may remain over the patient's scaphoid trapezium trapezoid (STT) joint. After the subsequent incision and the previous incision, the surgeon may expose the patient's dorsal capsule of the patient's CMC joint.

The surgeon may make a capsular flap incision in the patient's dorsal capsule, such that the surgeon exposes the patient's dorsal ridge of the patient's first metacarpal. The capsular flap incision may be substantially C-shaped, such that the capsular flap remains attached at a trapezial side of the patient's hand. The capsular flap may extend a distance between approximately 3 mm and approximately 4 mm on each side of the patient's dorsal ridge. However, the distance that the capsular flap may extend on each side of the patient's dorsal ridge may be greater than approximately 4 mm, or less than approximately 3 mm. The surgeon may locate, size, or otherwise make the capsular flap incision so as to prevent release of the proximal side of the patient's capsular flap from the patient's trapezium.

The surgeon may release other soft tissue adjacent to the patient's CMC joint, thereby allowing the surgeon to access the patient's CMC joint, the patient's trapezium, or the patient's first metacarpal.

The surgeon may resect at least a portion of the patient's first metacarpal. In some instances, the surgeon may resect a length of the patient's first metacarpal which is proximal to the patient's trapezium, and remove the resected portion of the patient's first metacarpal. In some instances, the surgeon may resect a section of the patient's first metacarpal which is distal to the patient's first metacarpal bump.

After resection of the patient's first metacarpal, the surgeon may insert and remove a temporary head implant between the resected end of the patient's first metacarpal and the patient's trapezium, and assess the joint laxity of the patient's CMC joint with the temporary head implant in place. In some instances, the surgeon may insert and remove a number of temporary head implants of different lengths between the resected end of the patient's first metacarpal and the patient's trapezium, one at a time, and reassess joint laxity for each of the temporary head implants. Accordingly, based on the length of the temporary head implant that will provide optimal post-operative results, the surgeon may determine the length of a permanent head implant that the surgeon will implant between the patient's first metacarpal and the patient's trapezium. For example, the surgeon may determine the length of the permanent head implant which will allow gentle circumduction of the patient's CMC joint without resistance or tension. Thereafter, the surgeon may remove the temporary head implant from between the resected end of the patient's first metacarpal and the patient's trapezium.

The surgeon may remove any metacarpal or trapezial osteophytes, such as osteophytes adjacent to the patient's first metacarpal, the patient's trapezium, or the patient's second metacarpal.

The surgeon may elevate the resected end of the patient's first metacarpal, to prepare the patient's first metacarpal for implantation of a component of the implant assembly, as further described. The surgeon may broach the elevated, resected end of the patient's first metacarpal, to form a hole in which the surgeon will implant a stem implant of the implant assembly.

The surgeon may implant the stem implant into the broached, resected end of the patient's first metacarpal. In some instances, the surgeon may implant one of multiple stem implants into the patient's first metacarpal, the surgeon choosing the stem implant based on a size of the broached hole in the resected end of the patient's first metacarpal, such that a size of the stem implant corresponds generally to a size of the broached hole. In some instances, no adhesive adheres the stem implant in the broached hole in the resected end of the patient's first metacarpal. In some other instances, an adhesive is used to adhere the stem implant within the broached hole in the resected end of the patient's first metacarpal.

The stem implant of the implant assembly may include a base portion configured to interface with the permanent head portion of the implant assembly, which the surgeon will implant between the stem implant and the patient's trapezium, the stem implant and the permanent head implant forming the implant assembly. In some instances, the surgeon may install the base portion in the stem implant prior to implantation of the stem implant in the resected end of the patient's first metacarpal. In some other instances, the base portion may be an integral part of the stem implant. In still some other instances, the surgeon may receive the stem implant with the base portion preinstalled. The surgeon may modify a surface of the patient's trapezium, such as for example to restore the usual hyperbolic-paraboloid or saddle-shape to the patient's trapezium. In some instances, the surgeon may use a rasp to modify the surface of the patient's trapezium. After implantation of the stem implant in the resected and broached end of the patient's first metacarpal, the surgeon may install the permanent head implant between the stem implant and the patient's trapezium.

Thereafter, the surgeon may begin a suturing procedure, as set forth with reference to the figures.

Figure 2:
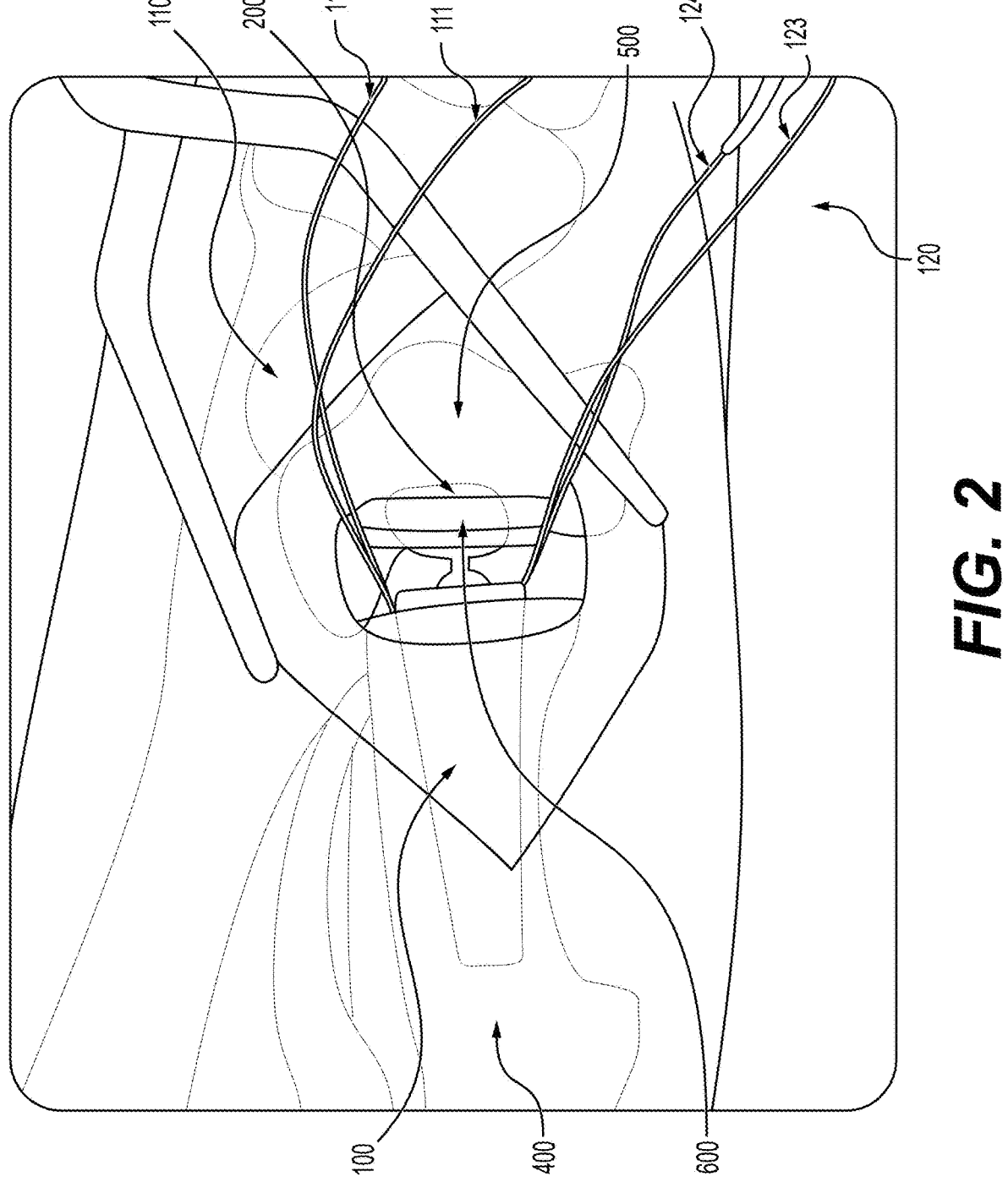
FIGS. 2-6 illustrate the suturing of a patient's capsular flap after implantation of the implant assembly in the patient's carpometacarpal (CMC) joint, in accordance with some aspects of the disclosure.

With reference to the drawings, FIGS. 1A and 1B illustrate a stem implant 100, and FIG. 2 illustrates a portion of a suturing procedure to be performed after the surgeon has made the substantially C-shaped cut in the patient's hand resulting in the substantially C-shaped capsular flap 600, and has implanted the stem implant 100 in the broached, resected end of the patient's first metacarpal 400, as well as implanted the permanent head implant 200 between the stem implant 100 and the patient's trapezium 500, in accordance with the above description. In FIG. 2, the patient's capsular flap 600 is in a retracted state, in which the patient's capsular flap 600 does not yet cover the implant assembly, for example. As FIGS. 1A, 1B, and 2 illustrate, the stem implant 100 includes two sutures each having two suture ends-a first suture 110 including a first suture end 111 and a second suture end 112, and a second suture 120 including a third suture end 123 and a fourth suture end 124. In some instances, the surgeon (or other medical personal) ties the first suture 110 and the second suture 120 around a portion of the stem implant 100 prior to implantation of the stem implant 100 in the patient's first metacarpal 400, such that the first suture 110 and the second suture 120 are anchored to the stem implant 100, and the first suture end 111 and the second suture end 112 are on an opposite side of the stem implant 100 than the third suture end 123 and the fourth suture end 124. In some instances, a kit includes the stem implant 100 and the first suture 110 and the second suture 120 separate from the stem implant 100. In some instances, the surgeon receives the stem implant 100 with the first suture 110 and the second suture 120 anchored thereon, such as by having been tied on the stem implant 100. The first suture 110 and the second suture 120 may be two double looped 4-0 braided sutures tied around a dorsal side of the stem implant 100, the first suture 110 and the second suture 120 being in a double-loop configuration on the stem implant 100. During implantation of the stem implant 100 by the surgeon in the broached, resected end of the patient's first metacarpal 400, the surgeon may hold the first suture 110 and the second suture 120 reasonably taut, such that the first suture 110 and the second suture 120 extend through the patient's capsular flap 600 as FIG. 2 shows.

Figure 3:

FIG. 3 illustrates the patient's capsular flap 600 in a folded down or closed state, with the first suture end 111 and the second suture end 112 of the first suture 110, and the third suture end 123 and the fourth suture end 124 of the second suture 120, extending through punctures in the patient's dorsal capsule. Specifically, as FIG. 3 shows, the surgeon arranges the first suture 110 and the second suture 120, such that the first suture end 111 and the third suture end 123 extend in different, generally opposite directions (for example, a first direction and a second direction) across the dorsal aspect of the implant site as well as over one another, before the first suture end 111 and the third suture end 123 extend through punctures in the patient's dorsal capsule. Accordingly, because the first suture end 111 and the third suture end 123 cross over one another, the first suture end 111 and the third suture end 123 interlock with one another. This arrangement of the first suture end 111 and the third suture end 123 over the implant assembly, including over the permanent head implant 200, stabilizes components of the implant assembly, including the stem implant 100 and the permanent head implant 200, during post-operative healing of the surgical site.

FIG. 3 further illustrates the second suture end 112 and the fourth suture end 124 longitudinally extending along the dorsal aspect of the implant site, from a distal end of the implant site to a proximal end of the implant site, before extending through punctures in the patient's dorsal capsule. Thus, both the second suture end 112 and the fourth suture end 124 longitudinally stabilize components of the implant assembly, including the stem implant 100 and the permanent head implant 200, during post-operative healing of the surgical site. In some instances, the second suture end 112 and the fourth suture end 124 extend through the punctures through which the third suture end 123 and the first suture end 11 extend, respectively. In some instances, the second suture end 112 and the fourth suture end 124 extend through different punctures other than the punctures through which the third suture end 123 and the first suture end 11 extend.

Figure 4:
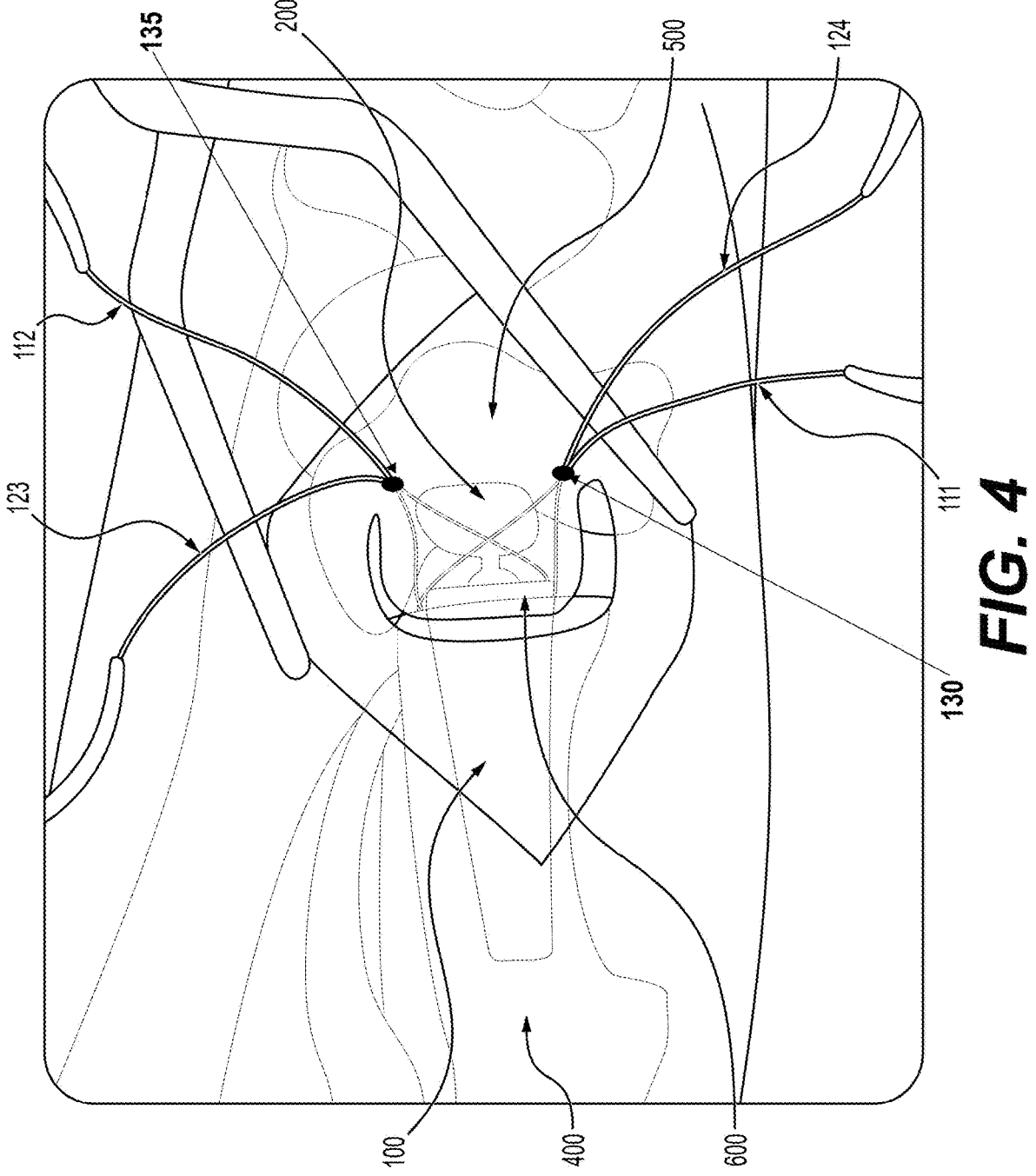

FIG. 4 is similar to FIG. 3, however FIG. 4 shows the first suture 110 and the second suture 120 after the surgeon ties and knots the first suture end 111 and the fourth suture end 124 with one another with a knot 130, and ties and knots the second suture end 112 and the third suture end 123 with one another with a knot 135. After knotting the suture ends with the knot 130 and the knot 135, the surgeon cuts the first suture end 111 and the third suture end 123 from the first suture 110 and the second suture 120, respectively.

Figure 5:
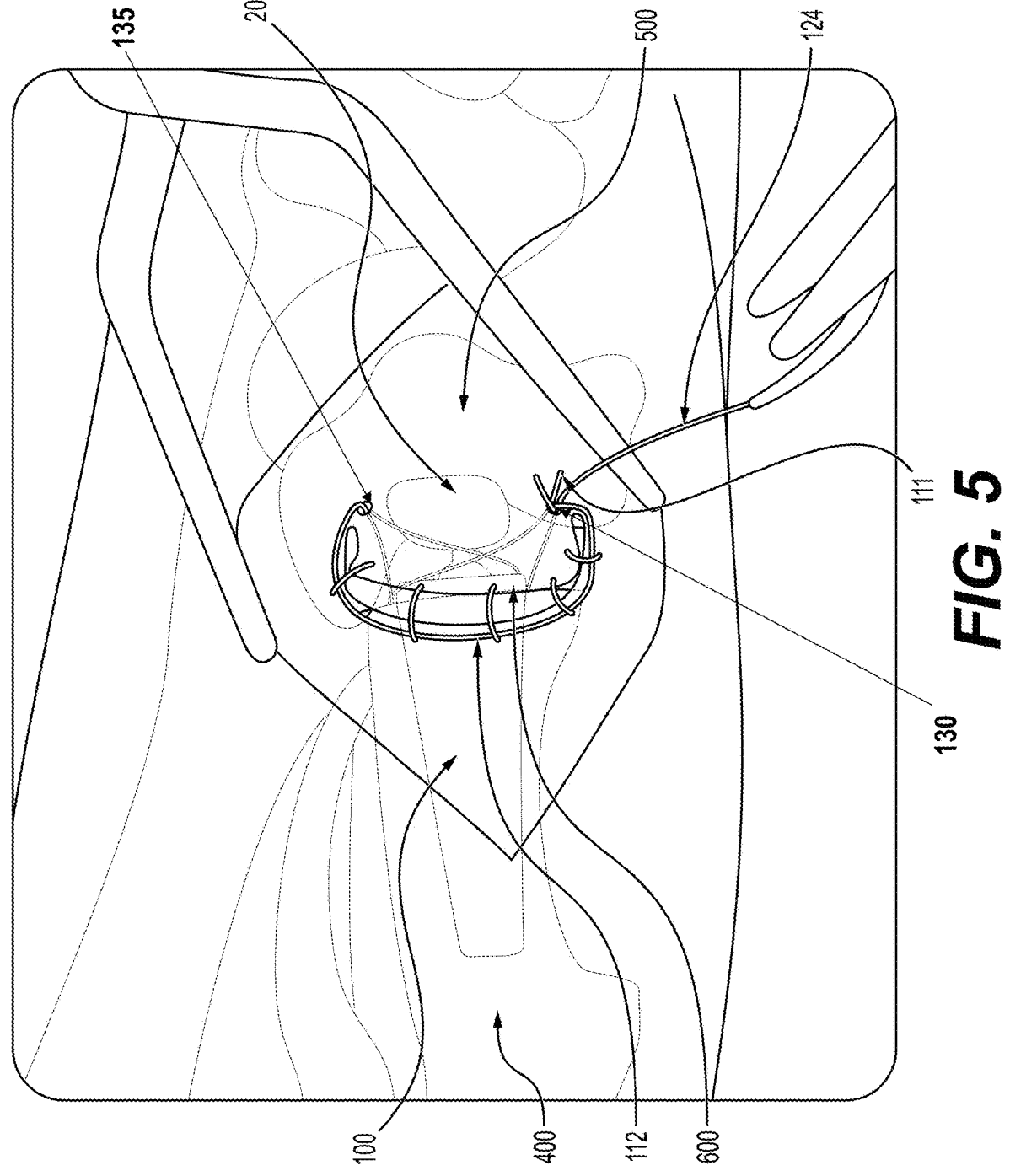

FIG. 5 illustrates the patient's capsular flap 600 initially sutured by the surgeon with the second suture end 112, after the surgeon has knotted the suture ends with the knot 130 and the knot 135, and has cut the first suture end 111 and the third suture end 123. As FIG. 5 illustrates, the surgeon sutures the patient's capsular flap 600 with the second suture end 112 in a first direction, which in the figure is counter-clockwise. As FIG. 5 further illustrates, the surgeon then ties off the second suture end 112, and cuts off the second suture end 112.

Figure 6:
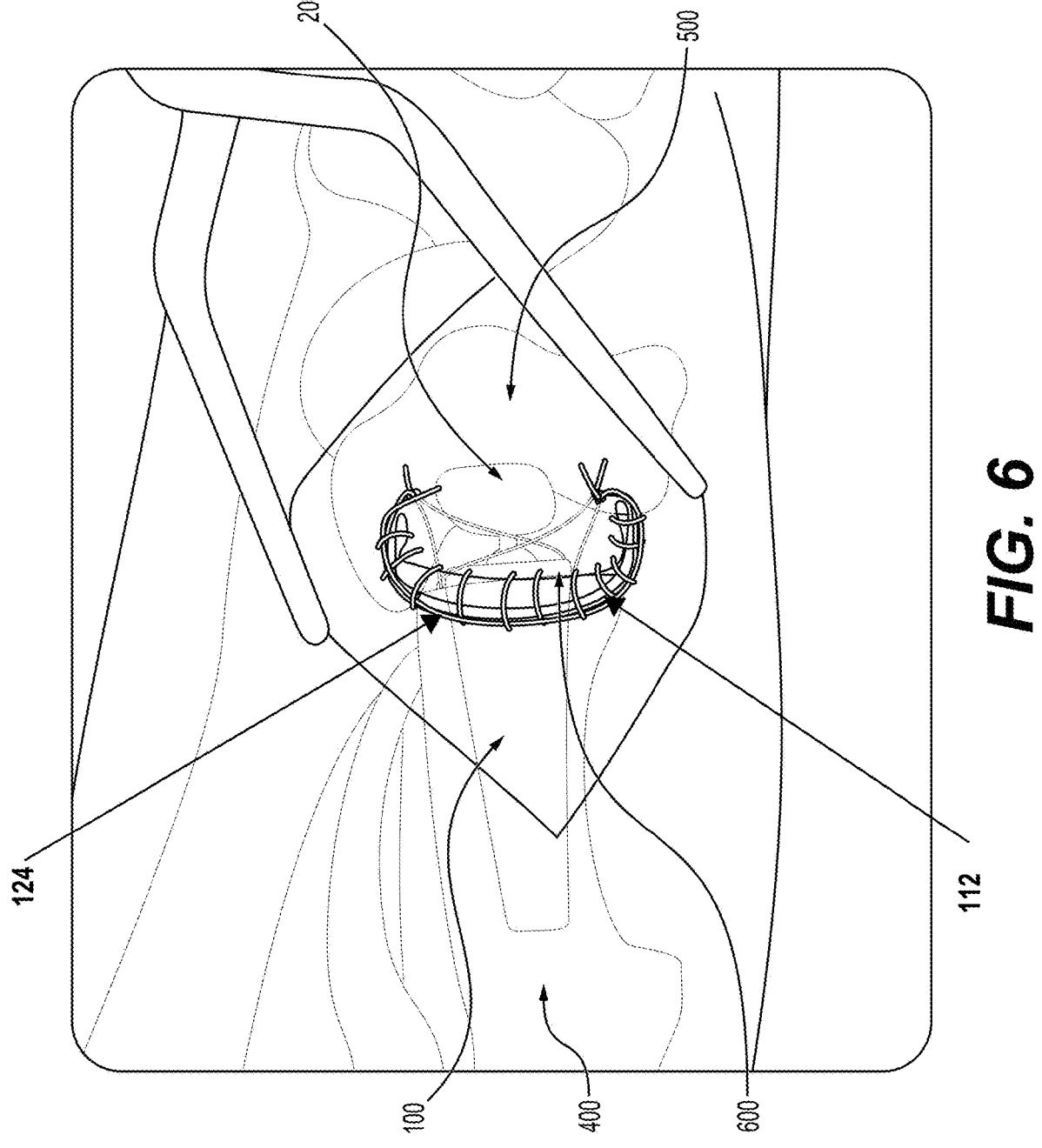

Thereafter, as FIG. 6 illustrates, the surgeon sutures the patient's capsular flap 600 with the fourth suture end 124. As FIG. 6 shows, the surgeon interweaves the fourth suture end 124 with the second suture end 112, such that the resulting suture configuration has a continuous pattern. As FIG. 6 illustrates, the surgeon sutures the patient's capsular flap 600 with the fourth suture end 124 in a second direction, which in the figure is clockwise. As FIG. 6 further illustrates, the surgeon then ties off the fourth suture end 124, and cuts off the fourth suture end 124. The interweaving pattern of the first suture 110 and the second suture 120 provides a reinforced closure of the patient's dorsal capsule. The interweaving pattern also minimizes gaps in the patient's dorsal capsule, and stabilizes the implant assembly during post-operative healing of the surgical site.

The described and illustrated suture configuration helps to seal and stabilize the patient's dorsal structure around the implant assembly, and assists in maintaining proper alignment between the patient's first metacarpal and the patient's trapezium, thereby reducing a risk of joint subluxation during post-operative healing. Further, the suture configuration may augment the dorsal retaining structure of the dorsal capsule, enhancing the stability of the implant assembly, and facilitating a secure closing of the wound over the implant site.

In some instances, the first suture 110 and the second suture 120 are absorbable sutures. In some other instances, the first suture 110 and the second suture 120 are non-absorbable sutures, and remain within the patient's hand after post-operative healing.

Figures 7, 8:
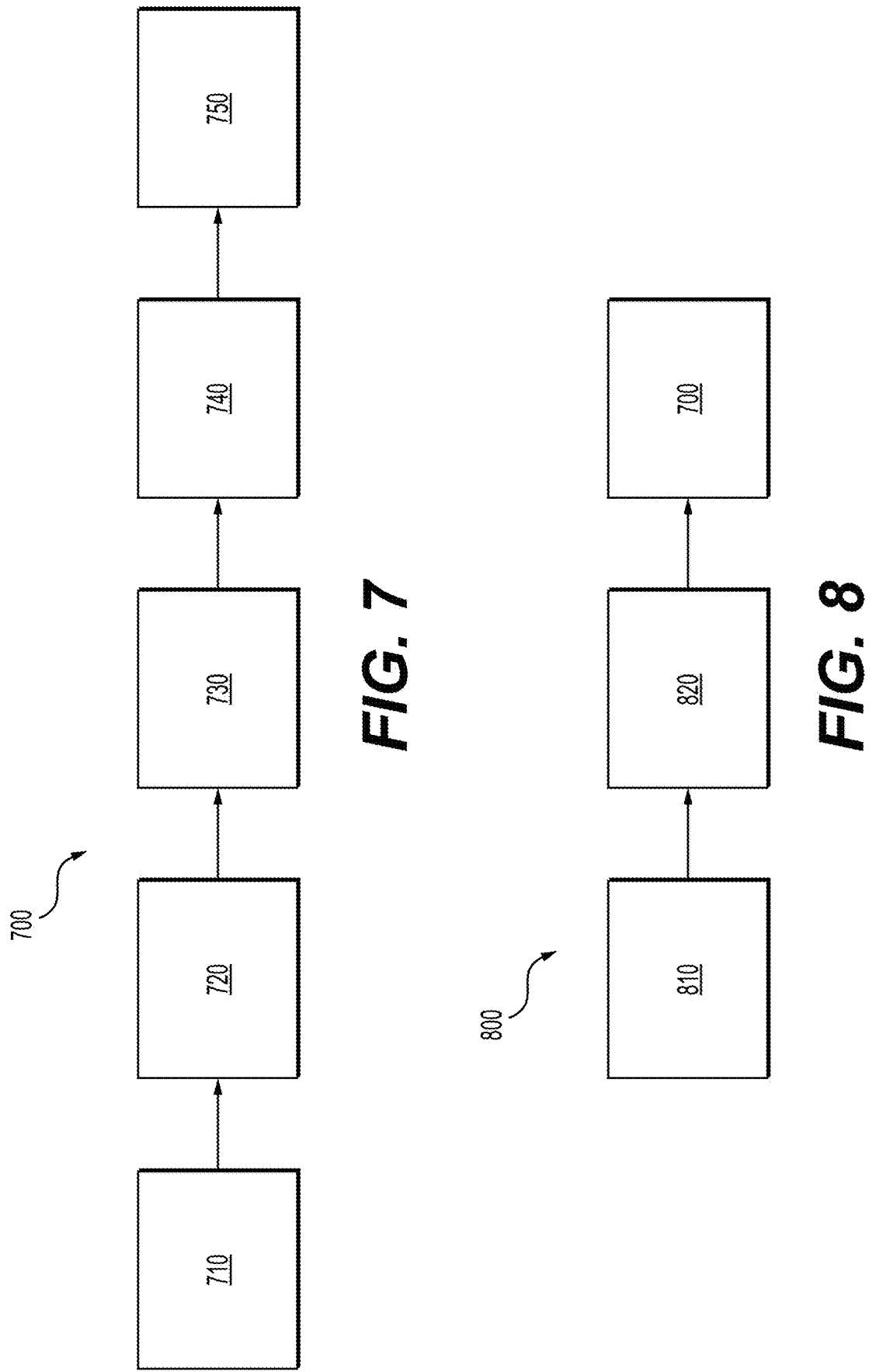
FIG. 7 is a flowchart illustrating an exemplary method of suturing, in accordance with some aspects of the disclosure.
FIG. 8 is a flowchart of an exemplary method of implanting the implant assembly, in accordance with some aspects of the disclosure.

FIG. 7 is a flowchart of an exemplary method of suturing, according to some aspects of the invention. The method 700 may include a method of suturing the surgical site after implantation, in the carpometacarpal (CMC) joint of the patient, of the implant assembly including the stem implant 100 and the permanent head implant 200, in which the first suture 110 and the second suture 120 anchored to the stem implant 100 extend from the stem implant 100. The method 700 may include a step 710, in which a suture end of the first suture 110, such as the first suture end 111, extends in a first direction across at least one component of the implant assembly (e.g., across either or both of the stem implant 100 or the permanent head implant 200), and through the patient's capsular flap 600. In some aspects, in the step 710, the first suture 110 may extend through a first puncture in the patient's capsular flap 600. The method 700 may include a step 720, in which a suture end of the second suture 120, such as the third suture end 123, extends in a second direction across the implant assembly, and through the patient's capsular flap 600, the suture ends crossing over one another. In some aspects, in the step 720, the second suture 120 may extend through a second puncture in the patient's capsular flap 600.

The method 700 may include a step 730, in which another suture end of each of the first suture 110 and the second suture 120, such as the second suture end 112 and the fourth suture end 124, respectively, extend through the patient's capsular flap 600. In some aspects, in the step 730, the second suture end 112 and the fourth suture end 124 do not cross over one another, over any other suture, or over any other suture end. In some aspects, in the step 730, the second suture end 112 and the fourth suture end 124 may extend through third and fourth punctures in the patient's capsular. In some aspects, in the step 730, the second suture end 112 and the fourth suture end 124 may extend through the second and first punctures in the patient's capsular flap 600, respectively. In some aspects, in the step 730, the first suture end 111 and the fourth suture end 124 are knotted with one another, and the second suture end 112 and the third suture end 123 are knotted with one another. In some aspect, in the step 730, the first suture end 111 and the third suture end 123 are cut after knotting.

The method 700 may include a step 740, in which at least one of the suture ends, such as at least one of the second suture end 112 or the fourth suture end 124, suture the patient's capsular flap 600. In some aspects, the step 740 may include suturing the patient's capsular flap 600 with both the second suture end 112 and the fourth suture end 124. In some aspects, the step 740 may include interweaving the second suture end 112 and the fourth suture end 124 with one another. In some aspects, the step 740 may include suturing the patient's capsular flap 600 with the second suture end 112 in a first direction (e.g., clockwise or counterclockwise) around a periphery of the patient's capsular flap, and suturing the patient's capsular flap 600 with the fourth suture end 124 in a second direction opposite to the first direction around a periphery of the capsular flap.

Thereafter, the surgeon may close the other incisions that the surgeon made previously in the patient's arm.

FIG. 8 is a flowchart of an exemplary method of implanting the implant assembly, according to some aspects of the invention. A method 800 may include a step 810, of implanting the stem implant 100 into a resected end of the patient's first metacarpal. The method 800 may include a step 820 of implanting the permanent head implant 200 between the stem implant 100 and the patient's trapezium of the patient. The method 800 may include the method 700 of suturing, subsequent to the step 810 and the step 820.

Thereafter, the surgeon may close the other incisions that the surgeon made in the hand of the patient.

It will be apparent to those skilled in the art that various modifications and variations may be made to the disclosed procedure without departing from the scope of the disclosure. Other embodiments will be apparent to those skilled in the art from consideration of the specification and practice of the procedure disclosed herein. The specification and examples are exemplary only, and the claims recite a true scope of the disclosure.

The invention claimed is:

1. A method of suturing a surgical site after implantation, in a carpometacarpal (CMC) joint of a hand of a patient, of an implant assembly including a first implant having a first suture and a second suture anchored thereto, the first suture and the second suture each secured to the first implant via a double-loop configuration, the first suture and the second suture extending from the first implant, the first suture including a first suture end and a second suture end, the second suture including a third suture end and a fourth suture end, the surgical site including a capsular flap that is substantially C-shaped and attached to a trapezial side of the hand of the patient, the method comprising:

extending the first suture end of the first suture in a first direction across the implant assembly and through a first puncture in the capsular flap;

extending the third suture end of the second suture in a second direction across the implant assembly and through a second puncture in the capsular flap, such that the first suture end and the third suture end cross over one another;

extending the second suture end of the first suture through the second puncture in the capsular flap; and extending the fourth suture end of the second suture through the first puncture in the capsular flap, wherein the second suture end and the fourth suture end do not cross over one another or any other suture end.

2. The method of claim 1, further comprising:

suturing the capsular flap of the patient with at least one of the suture ends.

3. The method of claim 1, further comprising:

suturing the capsular flap of the patient with at least one of the second suture end or the fourth suture end.

4. The method of claim 1, further comprising:

suturing the capsular flap of the patient with the second suture end; and suturing the capsular flap of the patient with the fourth suture end, wherein the second suture end and the fourth suture end interweave with one another.

5. The method of claim 1, further comprising:

suturing the capsular flap of the patient with the second suture end in a third direction; and suturing the capsular flap of the patient with the fourth suture end in a fourth direction, wherein the second suture end and the fourth suture end interweave with one another.

6. The method according to claim 1, wherein the implant assembly includes the first implant implanted within a resected and broached end of a first metacarpal of the patient, and the implant assembly further comprises a second implant implanted between the first implant and a trapezium of the patient, wherein the extending the first suture end of the first suture comprises extending the first suture end of the first suture over the second implant, wherein the extending the third suture end of the second suture comprises extending the third suture end of the second suture over the second implant.

7. The method of claim 1, further comprising:

suturing the capsular flap of the patient with the second suture end and the fourth suture end; and tying the first suture end with the third suture end, and the second suture end with the fourth suture end.

8. A method of suturing a surgical site after implantation, in a carpometacarpal (CMC) joint of a hand of a patient, of an implant assembly including a first implant implanted in a metacarpal of the patient, a second implant implanted between the first implant and a trapezium of the patient, the first implant having a first suture and a second suture anchored thereto, the first suture and the second suture extending from the first implant, the surgical site including a capsular flap that is substantially C-shaped and attached at a trapezial side of the hand of the patient, the method comprising:

extending a suture end of the first suture in a first direction across the second implant and through the capsular flap;

extending a suture end of the second suture in a second direction across the second implant and through the capsular flap, such that the suture ends cross over one another; and suturing the capsular flap with at least one suture end of the first suture or at least one suture end of the second suture.

9. The method of claim 8, wherein the suturing the capsular flap comprises suturing the capsular flap with suture ends of the first suture and the second suture.

10. The method of claim 8, wherein the first suture comprises two suture ends, wherein the second suture comprises two suture ends, wherein the suturing comprise suturing the capsular flap with only one suture end of the first suture and one suture end of the second suture.

11. The method of claim 8, wherein the first suture comprises two suture ends, wherein the second suture comprises two suture ends, wherein the suturing comprise suturing the capsular flap, in a third direction, with one suture end of the first suture and, in a fourth direction, with one suture end of the second suture.

12. The method of claim 8, further comprising:

extending another suture end of the first suture through the capsular flap without extending the suture end of the first suture over any portion of the implant assembly.

13. The method of claim 12, further comprising:

extending another end of the second suture through the capsular flap without extending over the suture end of the second suture any portion of the implant assembly or any other suture end.

14. The method of claim 13, wherein the suturing the capsular flap comprises suturing the capsular flap with at least one of the suture ends that does not extend over any portion of the implant assembly.

15. A method of implanting in a surgical site of a patient, in a carpometacarpal (CMC) joint of a hand of the patient, an implant assembly including a first implant and a second implant, the first implant including a first suture and a second suture anchored thereto, the first suture and the second suture extending from the first implant, the surgical site including a substantially C-shaped capsular flap attached at a trapezial side of the hand of the patient, the method comprising:

implanting the first implant into a resected end of a first metacarpal of the patient;

implanting the second implant between the first implant and a trapezium of the patient;

extending a suture end of the first suture in a first direction across the second implant and through a capsular flap of the patient; and extending a suture end of the second suture in a second direction across the second implant and through the capsular flap of the patient, such that the suture ends cross over one another.

16. The method of claim 15, further comprising:

suturing the capsular flap with another suture end of the first suture; and suturing the capsular flap with another suture end of the second suture, wherein the suture ends that suture the capsular flap interweave with one another.

17. The method of claim 15, wherein the first suture comprises a first suture end and a second suture end, wherein the second suture comprises a third suture end and a fourth suture end, wherein the extending the suture end of the first suture comprises extending the first suture end, wherein the extending the suture end of the second suture comprises extending the third suture end, wherein the method further comprises:

extending the second suture end and the fourth suture end through the capsular flap, wherein the second suture end and the fourth suture end do not cross over one another or any other suture end.

18. The method of claim 17, wherein the second suture end and the fourth suture end do not extend across the second implant.

19. The method of claim 17, further comprising:

suturing the capsular flap with the second suture end and the fourth suture end such that the second suture end and the fourth suture end interweave with one another.

20. The method of claim 15, further comprising:

resecting an end of the first metacarpal of the patient, to provide the resected end of the first metacarpal.

\* \* \* \* \*